United States Patent [19]

Sarig et al.

[11] 4,399,003

[45] Aug. 16, 1983

[54] METHOD AND KIT FOR DIAGNOSING A PATIENT'S PRONENESS TO DEVELOP CALCIUM OXALATE KIDNEY STONES

[75] Inventors: Sara Sarig; Nissim Garti, both of Jerusalem; Francoise Tibika, Ashdod, all of Israel

[73] Assignee: Yissum Research Development Company of the Hebrew University of Jerusalem, Jerusalem, Israel

[21] Appl. No.: 256,777

[22] Filed: Apr. 23, 1981

[30] Foreign Application Priority Data

May 2, 1980 [IL] Israel .................................... 59982

[51] Int. Cl.³ ............................................ G01N 27/46
[52] U.S. Cl. .................................... 204/1 T; 204/418; 422/61; 436/74; 436/79
[58] Field of Search ................ 204/1 A, 1 K, 195 R, 204/195 M; 23/230 B; 422/61, 68; 436/4, 74, 79, 150

[56] References Cited

U.S. PATENT DOCUMENTS 3,932,233  1/1976  Ruzicka et al. ................ 204/195 M
4,183,729  1/1980  Randolph ......................... 23/230 B Primary Examiner—G. L. Kaplan
Attorney, Agent, or Firm—Browdy and Neimark

[57] ABSTRACT

A method is provided for diagnosing a patient's proneness to develop kidney stones of the calcium oxalate type, which comprises forming an aqueous reaction medium comprising from about 5 to about 20% by volume of a sample of the patient's urine, said medium having an ionic strength of from about 0.01 to about 0.1 and containing calcium ions at a concentration of from about 1 to about 5 mM/l and oxalate ions at a concentration of from about 1 to about 7 mM/l; measuring by means of a calcium ion-specific electrode the rate of decrease of the calcium ion concentration and comparing the thus measured rate with the corresponding rate determined with a reference sample of normal urine. A kit for carrying out the above method is also provided.

11 Claims, 1 Drawing Figure

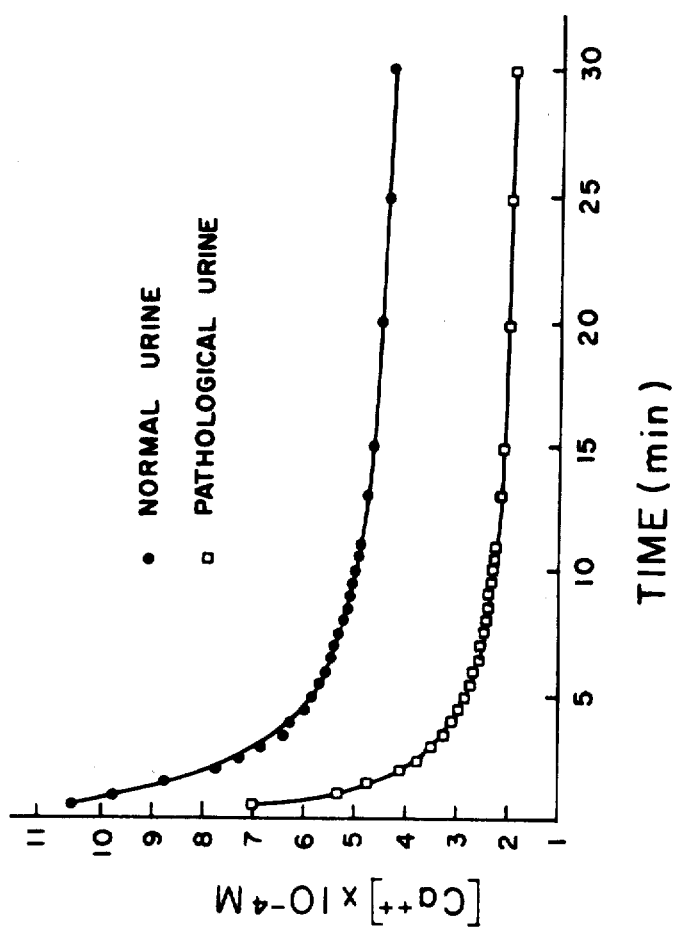

METHOD AND KIT FOR DIAGNOSING A PATIENT'S PRONENESS TO DEVELOP CALCIUM OXALATE KIDNEY STONES

The present invention provides a diagnostic method for determining a patient's proneness to develop kidney stones of the calcium oxalate type. The invention further provides a kit for carrying out the above diagnostic method.

The formation of stones in the kidneys is a severe and quite common pathological condition in humans which in a considerable percentage of the cases, may even result in death. Post-mortem examinations have revealed the presence of stones in the kidneys of more than 1% of the patients although many of them had never complained of any pathological symptoms. Human kidney stones may be classified into several types according to their chemical composition, e.g. calcium oxalate, calcium phosphate, uric acid, magnesium ammonium phosphate and cystein. The majority of the kidney stones, however, consist of calcium oxalate and considerable proportions of this compound are also contained in those kidney stones which consist mainly of calcium phosphate or magnesium ammonium phosphate.

Knowledge of the chemical type of kidney stones from which an individual patient suffers, is highly important for the medical treatment of such patient. Furthermore, recognition of an individual's propensity to develop stones of a certain chemical constitution, is essential for recommending prophylactic measures (such as a suitable diet) in order to retard or prevent the formation of such kidney stones. Hitherto, the chemical type of the kidney stones from which a patient suffers could only be determined with any degree of certainty by an actual chemical analysis of such a stone, either emitted from the patient's body in the urine or having been removed by surgery. Although the presence of kidney stones of certain chemical types, not including calcium oxalate, can be deduced from other indirect analytical and clinical data, such indirect indications are not conclusive and, as mentioned before, do not apply to the calcium oxalate stones which are the most frequent ones.

The object of the present invention is to provide a reliable method by which a patient's proneness to develop kidney stones of the calcium oxalate type can be diagnosed by performing a comparatively simple test with a sample of the urine of the patient, without the need to obtain and chemically analyse an actual kidney stone formed in the patient.

The present invention achieves the above object by providing a method of diagnosing a patient's proneness to develop kidney stones of the calcium oxalate type, which comprises forming an aqueous reaction medium comprising from about 5 to about 20%, preferably from about 7.5 to about 15% by volume of a sample of the patient's urine, said medium having an ionic strength of from 0.01 to 0.1 and containing calcium ions at a concentration of from about 1 to about 5 mM/l, preferably from about 1.5 to about 3 mM/l and oxalate ions at a concentration of from about 1 to about 7 mM/l, preferably from about 2 to about 4.5 mM/l; measuring by means of a calcium-specific electrode the rate of decrease of the calcium ion concentration and comparing the thus measured rate with the corresponding rate determined with a reference sample of normal urine, as herein defined.

The method of the invention is preferably performed by mixing in a vessel two aqueous solutions one of which provides for the required ionic strength and contains the required concentration of calcium ions (e.g. as calcium chloride) as well as the sample of the patient's urine, and the other containing the required concentration of oxalate ions (.e.g. as sodium oxalate). Thus, if equal volumes of the two solutions, say 50 ml. of each, are mixed, the solution of the calcium ions should comprise about 10 to about 40%, preferably about 15 to about 30% by volume of the urine sample. Conveniently the two solutions are introduced simultaneously into a glass vessel provided with a magnetic stirrer, with a calcium-specific electrode and with a suitable reference electrode. The activity of the free calcium ion in the medium is measured as a function of time and, preferably, plotted automatically by means of a conventional recording apparatus.

The term "concentration", in particular as applied to the calcium ion, is used herein interchangably with the more accurate term "activity", as a matter of convenience. It is clear that the calcium-specific electrode actually measures the activity of the calcium ions in the medium rather than their concentration.

The activity of the free calcium ions in the reaction medium decreases in line with the precipitation of calcium oxalate from the aqueous solution which is supersaturated with this salt, and after about 15 minutes, although the calcium ion activity continues to decrease, this decrease becomes extremely slow. It has been found that in the above reaction medium the calcium ion activity decreases much faster in the presence of a urine sample of a patient known to be suffering from calcium oxalate kidney stones, than the corresponding rate of decrease of calcium ion activity in the presence of a sample of "normal urine". In the case of "pathological urine" the calcium ion activity 30 minutes after the formation of the reaction medium was about half as large as the activity after 30 minutes in the case of normal urine, where in both cases the urine sample constituted 10% by volume of the total reaction medium.

It is known that human urine is super-saturated in respect of the calcium oxalate contained therein. The average concentration of calcium in the urine is of the order of $5 \times 10^{-3}$ M (about 200 mg/l) and the average concentration of oxalate ions in the urine is about $0.3 \times 10^{-3}$ M (about 30 mg/l). The product of these concentrations (about $1.5 \times 10^{-6}$) is much higher than the solubility product of calcium oxalate which is $2.1 \times 10^{-9}$ at 25° C. This phenomenon is observed in the urine of both healthy persons and persons suffering from calcium oxalate kidney stones. It is furthermore believed that in most cases, the formation of calcium oxalate stones in the kidneys is not necessarily accompanied by abnormally high concentrations of either calcium or oxalate in the urine. The present invention is based on the hypotheses that in normal persons the formation of calcium oxalate kidney stones, through crystallisation of calcium oxalate, is prevented by the presence in the urine of certain factors inhibiting the precipitation of calcium oxalate, notwithstanding the super-saturation of the urine in respect of this salt. It is assumed that these inhibiting factors are either absent in the urine of patients suffering from calcium oxalate kidney stones (herein "pathological urine") or that the inhibitory activity of these factors is impeded in some manner.

The reaction medium formed in accordance with the method of the invention emulates and even surpasses human urine in the degree of super-saturation with calcium oxalate. It has surprisingly been found in accordance with the invention, firstly, that the calcium ion activity in such a medium can reliably be measured with a calcium-specific electrode which is notorius for its sensitivity to even minute amounts of impurities. Secondly, it has been found that the presence of as little as 5% by volume of "normal urine" in this reaction medium suffices to considerably lower the rate of precipitation of calcium oxalate as indicated by the rate of decrease of calcium ion activity. As contrasted thereto, it has been found that the presence of "pathological urine" in the reaction medium in concentrations as high as 20% by volume, has practically no effect on the rate of decrease of calcium ion activity as compared to "blank tests" wherein the reaction medium contained no urine at all.

The term "normal urine" as used in the context of this invention refers to either urine taken from a person (or a mixed sample taken from a number of persons) not suffering from kidney stones of the calcium oxalate type, or to a sample of synthetic urine (is hereinafter defined) containing 100 ppm of poly-L-glutamic acid sodium salt, of molecular weight above 5000 (e.g. PGA-I, type I, Sigma Chemical Company), which is known to inhibit the precipitation of calcium oxalate. The inhibitory effect of such synthetic urine on the rate of decrease of calcium ion activity in a reaction medium formed in accordance with the invention, was found to be comparable to the effect of normal urine.

Synthetic urine suitable for use as a reference sample of "normal urine" (with the addition of 100 ppm of PGA-I) may suitably have the following composition:

| Concentration | g/l | $\times 10^{-3}$ M |
|---|---|---|
| Urea | 20 | 333 |
| Sodium sulphate | 2.27 | 16 |
| Potassium chloride | 4.84 | 65 |
| Sodium chloride | 5 | 85.5 |
| $NaH_2PO_4$ | 2.18 | 18 |
| Calcium chloride | 0.55 | 5 |

All the above components are dissolved in doubly distilled water.

The above composition is based on the work of Doremus et al (Invest. Urol. 15: 469 (1978), with the omission of creatin, hyppuric acid, ammonium chloride, magnesium ions and citric acid.

According to a preferred embodiment of the invention the aqueous reaction medium is formed by admixing equal volumes of a first solution consisting of synthetic urine of the above specified composition comprising from 10 to 40% by volume of the sample of the patient's urine, and a second solution consisting of a $6 \times 10^{-3}$ molar aqueous sodium oxalate solution.

The method according to the invention should preferably be carried out at a constant temperature, e.g. 25° C. or 37° C. To this end the reaction vessel may be placed in a thermostat.

In another aspect, the invention also provides a kit for carrying out the method of the invention, said kit comprising packaged synthetic urine solution and packaged aqueous sodium oxalate solution. The kit may further comprise one or more standard calcium chloride solutions for the calibration of the calcium-specific electrode. Further optional components of a kit according to the invention, are a calcium-specific electrode and a reference electrode.

The sole FIGURE is a graph showing calcium ion activity as a function of time in accordance with the results of Example 1, below.

The invention will now be illustrated by the following non-limiting example describing the performance of an actual test, with reference to the accompanying drawing.

EXAMPLE 1

A glass vessel in the form of a wide-mouthed jar having a volume of 250 cc. was placed in a water bath thermostat at a constant temperature of $25° \pm 1°$ C. The glass vessel was provided with a magnetic stirrer and with two electrodes, one of which was specific to calcium ions (ORION calcium ion electrode Model 93-20) and the other a suitable reference electrode of the double junction type (ORION double junction reference electrode Model 90-02). The potential difference between the calcium-specific electrode and the reference electrode was measured by means of a digital PH/mv meter. Prior to the actual test the calcium ion electrode was calibrated with the aid of standard solutions of calcium ions having concentrations of $10^{-2}$ M, $10^{-3}$ M and $10^{-4}$ M and having the same ionic strength as that of the reaction medium to be used according to the invention, at the same temperature of 25° C. These standard solutions were prepared by diluting a 0.1 M calcium chloride solution (ORION 0.1 M calcium standard solution No. 92.20.06), with a solution including suitable concentrations of all the above-specified components of synthetic urine, except for the calcium chloride.

Into the reaction vessel there were poured simultaneously equal volumes of 50 ml. each of the following two solutions:

(i) a mixture of 40 ml. of synthetic urine as hereinabove specified and 10 ml. of a sample of the patient's urine; and (ii) a $4 \times 10^{-3}$ M solution of sodium oxalate (C. P. Baker's analysed) in doubly distilled water.

The calcium ion activity in the resulting reaction medium was measured as a function of time over 30 minutes and the results were plotted as shown in the accompanying drawing, wherein the upper curve was obtained with a sample of normal human urine whereas the lower curve—with a sample of the urine of a patient suffering from calcium oxalate kidney stones. The attached drawing is clearly illustrative of the marked difference between the behaviour of the systems containing the normal and the pathological urine, respectively. It can further be seen therefrom that 30 minutes after the formation of the reaction medium, the calcium ion concentration in the medium containing the normal urine sample was $4.3 \times 10^{-4}$ M, whereas the corresponding concentration in the case of the pathological urine was $1.9 \times 10^{-4}$ M.

EXAMPLE 2

The procedure of Example 1 was used to test urine samples obtained from a population of 112 "oxalate stone formers" and 150 "controls", defined as follows:

"oxalate stone formers" as used herein refers to hospitalized patients who had undergone kidney stone extraction by surgery and whose stones were identified by chemical analysis as consisting exclusively or predominantly of calcium oxalate.

"Controls" in the present context refers to individuals who had never been treated for any urological complaint and who consider themselves healthy. (Among the controls tested were a group of young students).

The results were expressed as percent reduction of calcium ion activity 10 minutes after the admixture of the two solutions in the reaction vessel, as described in Example 1. These percentage values were processed statistically and the standard deviations (for each of the sets of results of the oxalate stone formers and the controls) were calculated.

The average percent reduction of calcium ion activity values obtained were as follows:

Oxalate stone formers: 75% ± 3.4
Controls: 31% ± 3.3

The two average values differ by more than twice the sum of the two deviation values (for each curve of distribution of values).

We claim:

1. A method of diagnosing a patient's proneness to develop kidney stones of the calcium oxalate type, which comprises forming an aqueous reaction medium comprising from about 5 to about 20% by volume of a sample of the patient's urine, said medium having an ionic strength of from about 0.01 to about 0.1 and containing calcium ions at a concentration of from about 1 to about 5 mM/l and oxalate ions at a concentration of from about 1 to about 7 mM/l; measuring by means of a calcium ion-specific electrode the rate of decrease of the calcium ion concentration and comparing the thus measured rate with the corresponding rate determined with a reference sample of normal urine, as herein defined.

2. A method according to claim 1, wherein the reaction medium comprises from about 7.5 to about 15% by volume of the sample of the urine.

3. A method according to claim 1, wherein the concentration of calcium ions in the reaction medium is from about 1.5 to about 3 mM/l.

4. A method according to claim 1, wherein the concentration of oxalate ions in the reaction medium is from about 2 to about 4.5 mM/l.

5. A method according to claim 1, wherein the reaction medium is formed by admixing a first aqueous solution comprising the calcium ions, other ions providing for the required ionic strength and the sample of the patient's urine, with a second aqueous solution containing the required concentration of oxalate ions.

6. A method according to claim 5, wherein equal volumes of said first and said second solutions are admixed.

7. A method according to claim 5, wherein said first solution consists of from about 60 to about 90% by volume of synthetic urine, as herein defined, and from about 10 to about 40% by volume of the sample of the patient's urine.

8. A method according to claim 1, wherein the oxalate ions are derived from sodium oxalate.

9. A method according to claim 1, wherein the normal urine used as a reference sample is synthetic urine as herein defined, to which were added 100 ppm. of poly-L-glutamic acid sodium salt of molecular weight above 5000.

10. A method according to claim 1, which is carried out at a temperature of 25° C.

11. A kit for carrying out the method according to claim 1, said kit comprising packaged synthetic urine solution and packaged aqueous sodium oxalate solution, and further comprising a calcium ion-specific electrode and a reference electrode.

* * * * *